US006648885B1

(12) United States Patent
Friesem

(10) Patent No.: US 6,648,885 B1
(45) Date of Patent: Nov. 18, 2003

(54) DEVICE FOR THE OSTEOSYNTHESIS OF A SPINAL SEGMENT

(75) Inventor: Tai Friesem, Kfar-Saba (IL)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/831,670

(22) PCT Filed: Nov. 11, 1999

(86) PCT No.: PCT/IB99/01813
§ 371 (c)(1),
(2), (4) Date: May 11, 2001

(87) PCT Pub. No.: WO00/28905
PCT Pub. Date: May 25, 2000

(30) Foreign Application Priority Data

Nov. 12, 1998 (FR) .............................. 98 14210

(51) Int. Cl.[7] .............................. A61B 17/70
(52) U.S. Cl. .......................... 606/61; 606/69
(58) Field of Search ................. 606/60, 61, 69–73

(56) References Cited

U.S. PATENT DOCUMENTS 5,152,303 A * 10/1992 Allen ..................... 128/898
5,180,381 A * 1/1993 Aust et al. ................ 606/61
5,330,477 A * 7/1994 Crook ..................... 606/69
5,709,686 A * 1/1998 Talos et al. ............... 606/69
6,106,527 A * 8/2000 Wu et al. .................. 606/61
6,395,030 B1 * 5/2002 Songer et al. ........... 623/17.11
6,478,795 B1 * 11/2002 Gournay et al. ............ 606/61
6,520,990 B1 * 2/2003 Ray ....................... 623/17.11

* cited by examiner

Primary Examiner—Kevin Shaver
Assistant Examiner—Michael B. Priddy
(74) Attorney, Agent, or Firm—Woodard, Emhardt, Moriarty, McNett & Henry LLP

(57) ABSTRACT

Device for the osteosynthesis of a spinal segment by the anterior route, which comprises at least two bone anchorage elements for anchorage in the vertebral bodies by the anterior route, a frame comprising a rod adapted to be received in the bone anchorage elements, a plate disposed roughly parallel to the rod and rigidly connected to the latter to form a closed frame. Means are provided for clamping the rod in the anchorage elements so as to fix the latter at a predetermined distance apart, and screws extend through openings in the plate which are so profiled that the screwing of the screws in the vertebrae automatically brings the two adjacent vertebrae closer together and thus achieves a compression of an intervertebral filler replacing a vertebral disk. The association of a plate and a rod in the form of a frame affords the advantage of providing four vertebral anchorage points instead of only two in devices of the prior art, which prevents any offsetting of one vertebra relative to the other.

30 Claims, 4 Drawing Sheets

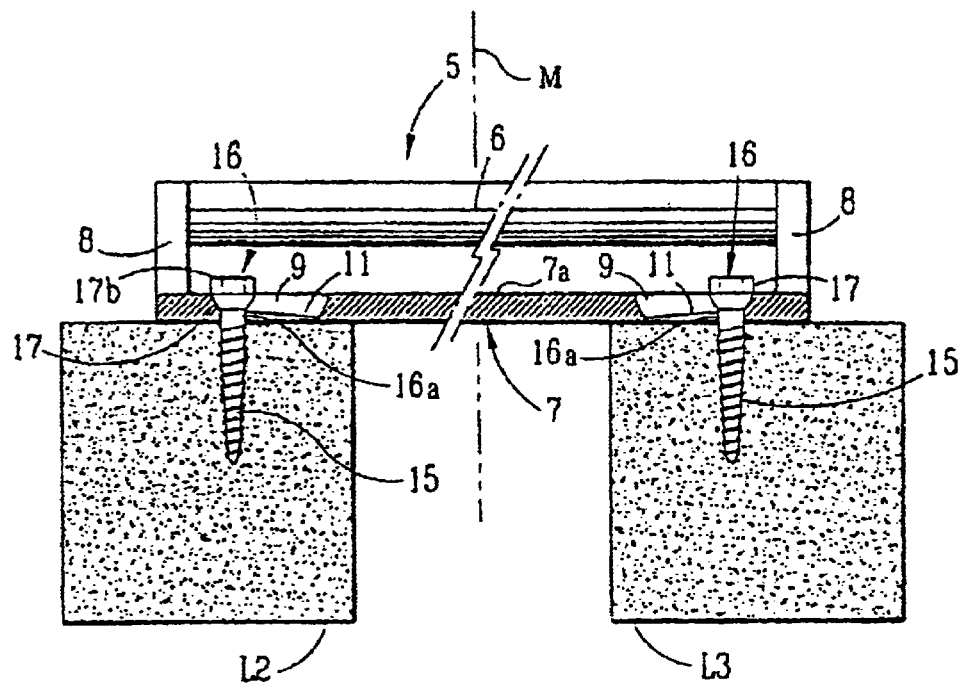
FIG.7
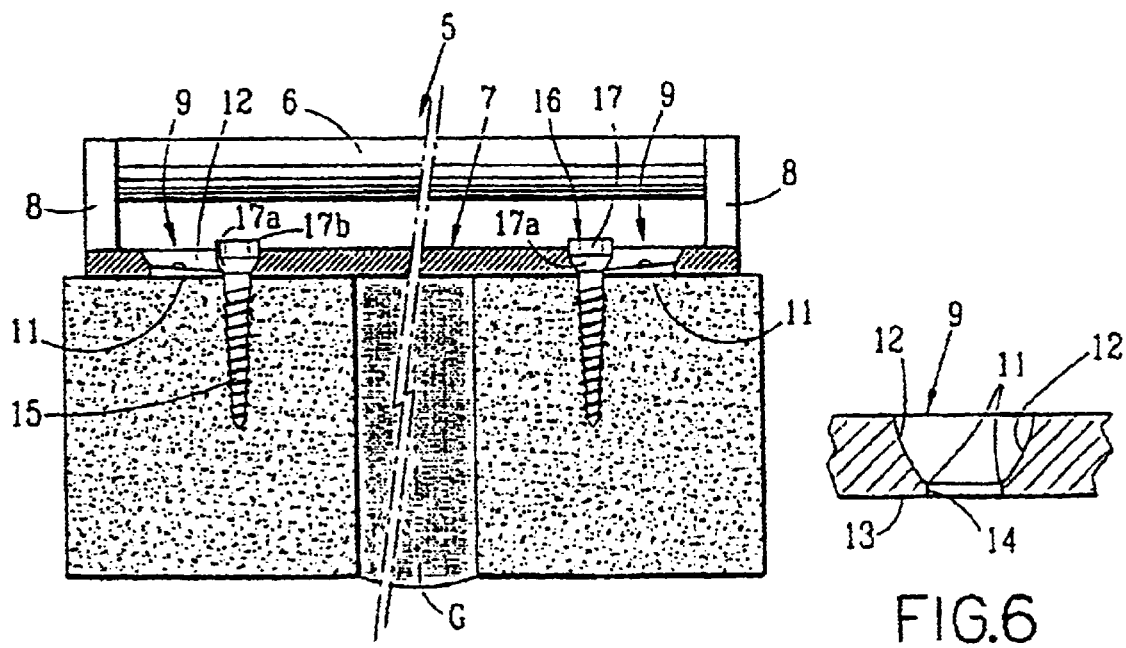
FIG.8
FIG.6

DEVICE FOR THE OSTEOSYNTHESIS OF A SPINAL SEGMENT

BACKGROUND OF THE INVENTION

The present invention relates to a device for the osteosynthesis of a spinal segment and more particularly, but not exclusively, a device for osteosynthesis of the spine by the anterior route for the correction of vertebral deformations and degenerations. Among portions of the spine to which these devices may be particularly adapted include the thoracic, thoraco-lumbar, and lumbar spinal segments.

Systems are known in the art which employ rods alone, plates alone, and rod-plates interconnected in such a manner that the plate extends the rod substantially on the longitudinal axis of the latter. Thus the U.S. Pat. No. 5,507,745 describes a rod-plate adapted for an occipito-cervical assembly. The document EP 0,553,042 also teaches the use of a device of the rod-plate type, the plate being in the extension of the longitudinal axis of the rod, this system being particularly adapted for the lumbar-sacral articulation. Once drawback of such rod-plate systems resides in the fact that one of the vertebrae may become undesirably offset relative to the other.

In conventional open surgical interventions involving the removal of a disc, a fusion cage or a graft is placed in position to restore the discal height, and then the two adjacent vertebrae are compressed manually for maintaining in place the bone graft or the cage. Within the framework of the development of surgical interventions by endoscopy and by the anterior route (i.e. with a small-section abdominal opening through which trocars and a closed-circuit microtelevision camera are inserted), the compression of the two vertebrae presents a particular difficulty. Heretofore, the surgeons did not add a material or content themselves to stabilize the instrumentation. Thus, there is a need for devices and methods to address these shortcomings.

SUMMARY OF THE INVENTION

One form of the present invention is a unique medical treatment device. Other forms include unique osteosynthesis devices and methods.

In another form of the present invention, an osteosynthesis device comprises a rod and a plate disposed substantially parallel to the rod and rigidly connected to the same, and bone anchoring means for engaging the rod and the plate to a spinal segment. Such a system can be equipped with four anchoring elements to address problems regarding relative displacement between vertebrae.

In a further form, a device according to the invention extends over a spinal segment of at least two vertebrae. A surgeon extracts the defective intervertebral disk and then inserts, instead of the disk, a filler, which can be, for example, a bone graft or one or more intersomatic cages. A compression of the graft or the cages is performed to thereby bring the two vertebrae closer together, which vertebrae are thereafter fixed in position.

According to another form, the device comprises means cooperative with the plate for bringing closer together two adjacent vertebrae into each of which an anchorage element is placed; whereby to effect a compression of a filler between the two vertebrae which replaces a removed vertebral disk.

A further form of the invention includes a plate and a rod interconnected at their facing ends by lugs forming with the rod and the plate a substantially rectangular frame, and means for bringing two adjacent vertebrae closer together. Such means may comprise a pair of oblong openings formed in the plate that extend in a direction parallel to the rod in facing relation to each vertebra, and screws adapted to be anchored in the corresponding vertebral body through said openings, the latter and the screws being so arranged that the progressive screwing of the screws brings the two vertebrae closer together. The openings each have a wall defining at its base a ramp which slopes toward the central part of the plate and in the direction toward the surface of the plate bearing against the vertebrae. For this form, the wall/ramp arrangement is formed of a succession of spherical segments and is connected by a cylindrical portion to the bearing surface, and the screws associated with these openings have heads arranged to engage the walls.

Accordingly, one object of the Invention is to provide devices and method for medical treatment procedures.

Another object is to provide a device for osteosynthesis arranged in such a manner as to facilitate compression of adjacent vertebrae.

Further objects, forms, embodiments, aspects, benefits, features, and advantages of the invention will be clear from the following description with reference to the accompanying drawings which illustrate several embodiments of the invention by way of non-limiting examples.

BRIEF DESCRIPTION OF THE DRAWINGS

FIG. 6 is a partial sectional view taken along section line 6—6 of FIG. 2.

FIG. 7 is a longitudinal elevational view in a sagittal plane of the osteosynthesis assembly of FIGS. 1 to 6 placed in position on two vertebrae spread apart after extraction of the intervertebral disk.

FIG. 8 is a view similar to FIG. 7 showing the two vertebrae brought closer together and the compression of the bone graft and/or intersomatic cage after the screwing of the screws of the plate into the two vertebrae.

DESCRIPTION OF SELECTED EMBODIMENTS

Figure 1:
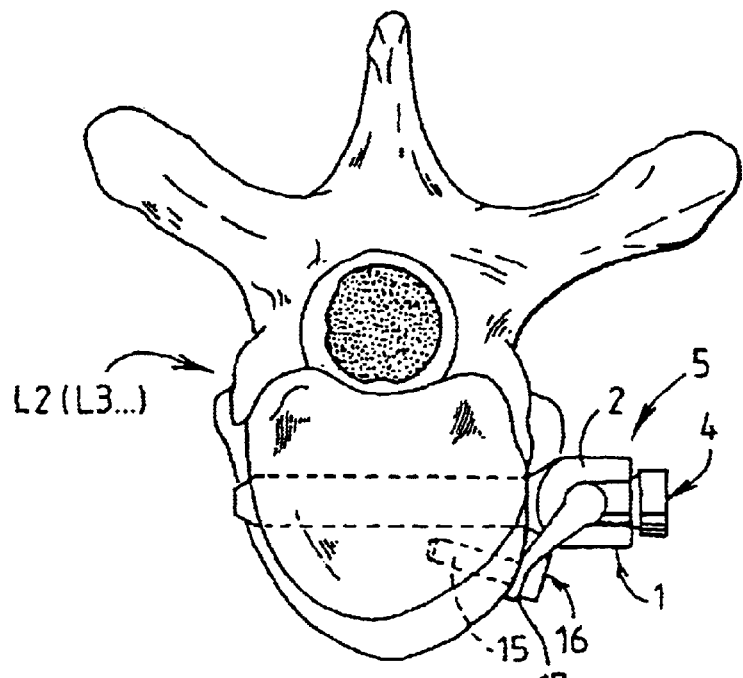
FIG. 1 is a view of a vertebra substantially to scale in a horizontal plane and a top end elevational view of an embodiment of the spinal osteosynthesis assembly according to the invention in position in this vertebra.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 5:
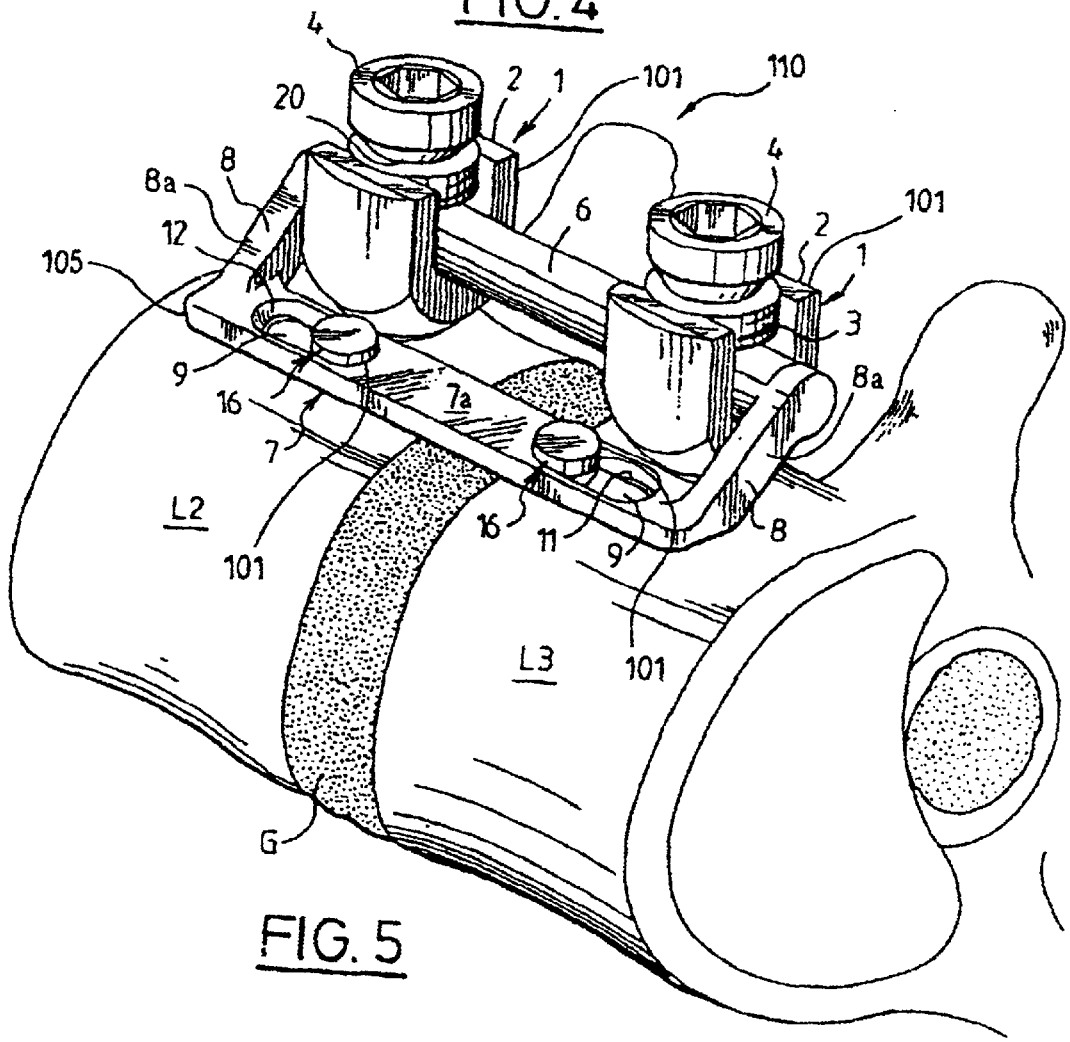
FIG. 5 is a perspective view to a larger scale of the assembly for osteosynthesis by the anterior route of FIGS. 1 to 4 anchored on a spinal segment of two vertebrae.

FIG. 5 illustrates device 110 of one embodiment of the present invention. Device 110 may be for the osteosynthesis of a spinal segment formed, for example, by two lumbar or thoracic vertebrae L3, L2 placed in position by the anterior route. Device 110 includes a number of bone anchorage elements 101, four of which are illustrated in FIG. 5 as a pair of screws 1 and a pair of screws 16. At least two bone anchorage elements, such as two screws 1, are for anchoring in the corresponding vertebral bodies; these screws 1 may be for example, of the type having a U-shaped head 2 the inner faces of which are threaded or tapped for receiving a clamping element in the form of threaded plug 3 provided with a terminal portion 4 which may be broken off at fracture line 20 by exerting a predetermined fracture torque. Such a clamping element is described in French patent No. 2,723, 837 (94,10,377), the disclosure of which is incorporated in the present specification by reference. Nonetheless, in other embodiments,, terminal portion 4 may not be frangible.

Device 110 also includes an implant structure 105 provided in the form of frame 5. Frame 5 is comprised of rod 6 interconnected to plate 7 by connection members 8a. Rod 6 is preferably cylindrical and adapted to be received in the U-shaped heads 2 of the anchorage screws 1, by bearing against the bottom of the U-shaped passage, and clamped in position by the threaded plugs 3. Accordingly, rod 6 may be fastened to screw 1 between U-shaped head 2 and plug 3. Plate 7 is disposed approximately parallel to rod 6 and extends therealong. Plate 7 is substantially of the same length as rod 6, and rigidly connected to the latter in a side by side relationship to form frame 5 in a closed configuration.

Figure 2:
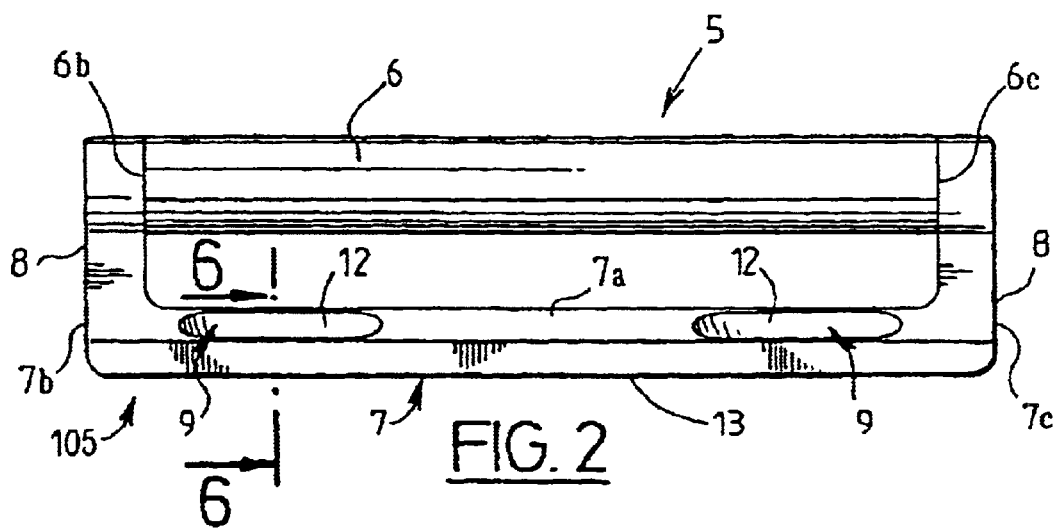
FIG. 2 is a longitudinal elevational view to a larger scale of the rod-plate frame forming part of the osteosynthesis assembly of FIG. 1.
Figure 3:
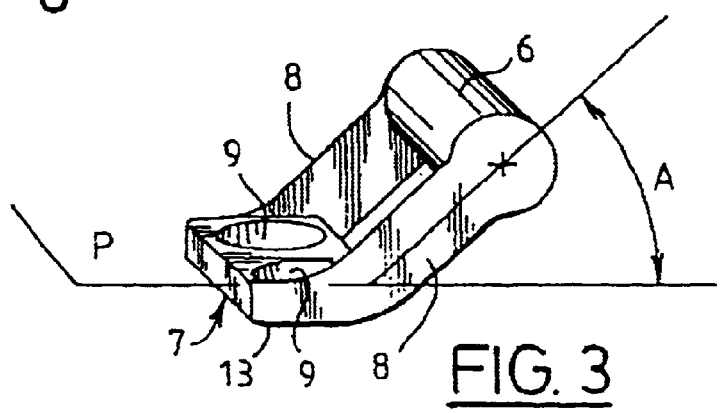
FIG. 3 is a perspective view of the rod-plate frame of FIG. 2.
Figure 4:
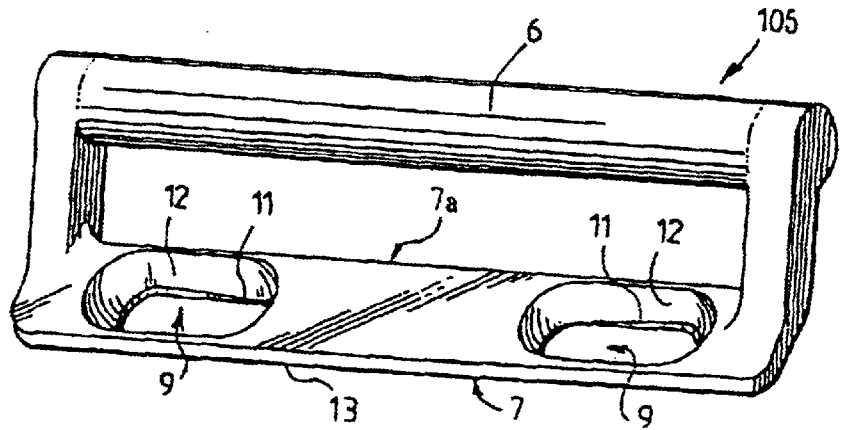
FIG. 4 is a perspective view in another direction of the rod-plate frame of FIG. 3, showing more particularly the oblong openings in the plate.

Referring additionally to FIGS. 2–4, plate 7 and the rod 6 are interconnected at their opposite end portions 7b, 7c and 6b, 6c, respectively; by a number of connection members 8a in the form of lugs 8 constituting with the rod 6 and the plate 7 a substantially rectangular shape or profile of frame 5. Preferably, lugs 8 each have a longitudinal axis that is inclined at a given angle A relative to the plane P along which plate 7 lies, for example at between about 30 and about 45° (FIGS. 3 and 5), so that the rod 6 is offset relative to the plane P of the plate 7. Plane P is generally parallel to a longitudinal axis of plate 7. Lugs 8 may be either in one piece with the rod 6 and/or plate 7 or detachably fixed to rod 6 and/or plate 7 by any suitable means. For example, the ends of one or more of the lugs 8 remote from the plate 7 may be arranged in the shape of a cup for fitting onto the ends of rod 6 to which they are fixed by any suitable means, which permit, if required, removing lugs 8 from rod 6. In other embodiments, one or more of lugs 8 may be releasably fastened at plate 7. In still other embodiments, a fixed spatial relationship between rod 6 and plate 7 may be maintained by members 8a; however, rod 6 may be allowed to rotate between lugs 8.

Arranged in plate 7 is at least a pair of oblong openings 9 which extend in a direction parallel to rod 6 in facing relation to the intended position of each vertebra, such as L2, L3. Each opening 9 has a wall 12 defining at its base adjacent to the corresponding vertebra L2 or L3, at least one ramp 11, preferably two ramps 11 as in the illustrated embodiment (a ramp 11 for each wall 12), which slopes toward the central part 7a of the plate 7 and in the direction toward the surface 13 of the plate 7 bearing against the vertebrae L2, L3. Referring more specifically to FIGS. 4, 7, and 8, the two pairs of ramps 11 of the two openings 9 thus have respective slopes at a relatively small angle, for example 8° to 10°, which converge toward axis M as shown in FIG. 7.

Referring next to FIGS. 5–8, in the direction away from the bearing surface 13, each ramp 11 adjoins a surface constituting the wall 12 which is formed, when viewed in cross section (FIG. 6), of a succession of spherical segments. At the lower ends of the latter, the ramps 11 form edges from which a short cylindrical portion 14 extends to the bearing surface 13. This profile corresponds to and is adapted to mate with that of a head 17 of a screw 16 having a spherical portion 17a. Head 17 is connected to an unthreaded intermediate portion 16a of screw 16. Portion 16a is connected to threaded shank 15 of screw 16. Head 17 of screw 16 also is extended by a terminal polygonal profile 17b, for example a hexagonal profile, opposite threaded shank 15.

The profile of openings 9 may be provided by machining with a correspondingly shaped rotating member (not shown) which travels from one end to the other of each opening 9 as it machines the spherical walls 12 and the ramps 11 at the required slope. Associated with these profiled openings 9 are respective screws 16 each having a spherical head 17 with spherical portion 17a. Spherical portion 17a has a radius of curvature which is substantially equal to that of spherical segments of wall 12, so that the heads 17 of the screws 16 (FIGS. 7 and 8) can slide from one end to the other of the ramps 11 as the screws 16 are progressively screwed into the respective vertebrae L2, L3.

The spinal osteosynthesis device just described is preferably mounted in the following manner:

(a) The surgeon places the two screws 1 in position by anchoring them by the anterior route into the selected vertebrae, for example L2 and L3.

(b) He disposes the cylindrical rod 6 in the heads 2 of the screws 1 and places the plugs 3 in position in the heads 2, respectively;

(c) The surgeon then places the plate 7 of the frame 5 against the vertebral bodies and inserts the screws 16 in the outer ends of the opening 9 where the heads 17 bear against the uppermost ends of the ramps 11 (FIG. 7), and screws 16 are turned until they bear against the ends of the spherical walls 12 and of the ramps 11, taking care to approximately direct the threaded shanks 15 toward the center of gravity or centroid of the vertebrae, which facilitates the subsequent compression; and (d) The surgeon completes the screwing of plugs 3 until the self-breaking terminal portions 4 break off along their fracture line 20 (FIG. 5) when the predetermined fracture torque is reached. The placing in position of the system for the spinal osteosynthesis by the anterior route for this embodiment has now finished. It should be understood that while placement by an anterior route is preferred for this embodiment, in other embodiments a different placement route may be utilized. Likewise, the devices of the present invention may be used with endoscopic and/or non-endoscopic procedures.

It is envisioned that screws 16 may be self-cutting or not self-cutting. In the case where the screws 16 are self-cutting, the surgeon screws them directly into the vertebral bodies without raising the plate 7. As the screws 16 are progressively screwed, the heads 17 contact and slide along the spherical walls 12 and the ramps 11 in the direction toward the center part of plate 7, which causes the vertebrae L2, L3, driven along by the screws 16, to move toward each other. This movement toward each other and the corresponding compression of a filler G (see FIGS. 5 and 8); such as an osteogenic material, an intervertebral graft, or intersomatic cage(s) disposed in the intervertebral space; stops when the surgeon thinks filler G is sufficiently compressed. In the case where the screws 16 are not self-cutting, the surgeon first raises the plate 7, drills and taps the openings for the screws (after optionally having center-punched the exact position of the latter). He then places the plate 7 back against the vertebrae and screws the screws 16, with a corresponding movement of the vertebrae closer together and compression of filler G.

The arrangement of the oblong openings 9 with their spherical walls 12 and their ramps 11 so inclined as to converge toward the center part 7a of plate 7, permits bringing the vertebral bodies closer together and consequently automatically compressing filler G as the screws 16 are progressively screwed into position. This is but one advantage within the framework of a surgical intervention by endoscopy. Another appreciable advantage of device 110 according to the invention results from the association of the rod 6 and plate 7 in parallel to form frame 5. Indeed, the latter provides four vertebral anchorage points (the four screws 1 and 16) which reduce displacement or offsetting of one vertebra relative to the other. Still, in other embodiments, a different number of screws and corresponding openings may be utilized.

Figure 9:
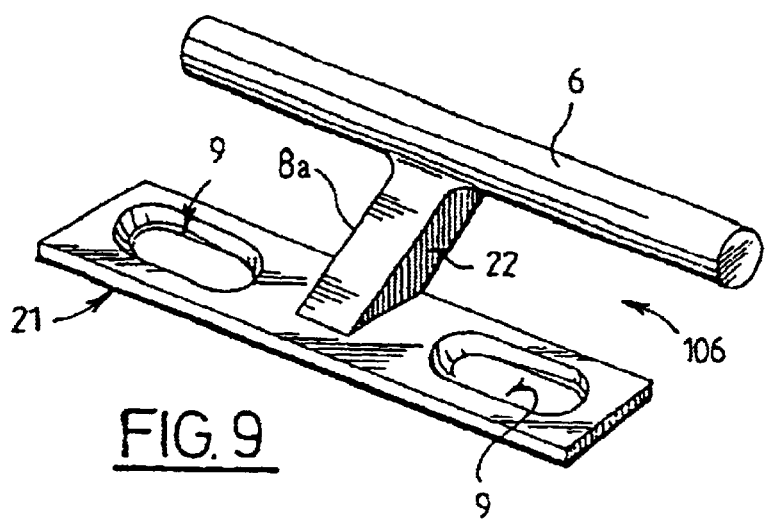
FIGS. 9 and 10 are perspective views illustrating two other embodiments of the rod-plate system according to the invention.

In the alternative embodiment of FIG. 9, rod 6 is rigidly connected to plate 21 in their respective central parts by another type of connection member 8a, strut 22, so that the assembly generally defines a rigid H-shaped structure 106.

Figure 10:
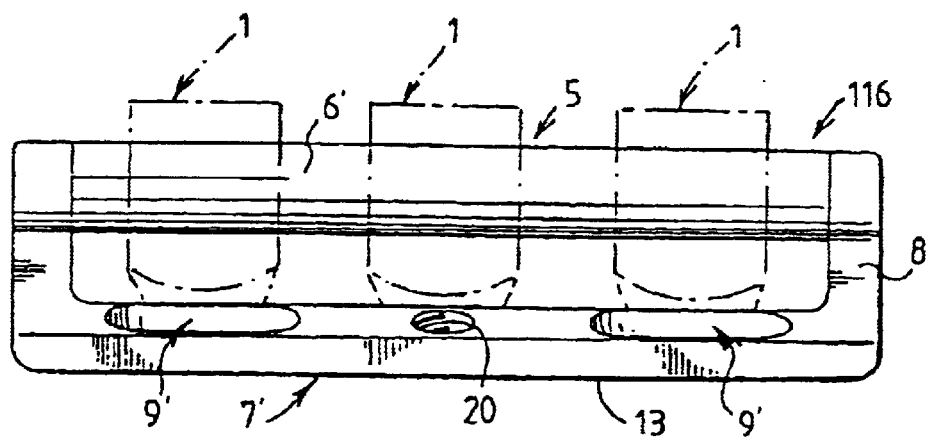

FIG. 10 illustrates implant structure 116 of a further embodiment of the present invention. For structure 116, rod 6' and the plate 7' are interconnected to extend upon a length corresponding to a spine segment of three vertebrae. For this embodiment, three bone anchorage screws 1 are shown in phantom, one for each of the three vertebrae. The plate 7' is provided in its central part with a bone anchoring element hole 20 aligned with the central vertebra. On each side of the central part, the plate is pierced with oblong openings 9' accommodating screws 16. The central screw is used for fixing the frame 6'/plate 7' on the central vertebra. The screwing of screws 16 into openings 9' brings progressively both end vertebrae closer to the central vertebra until the surgeon thinks that the graft is sufficiently compressed. In an alternative embodiment, this arrangement can be designed on the embodiment of FIG. 9, in order that the assembly rod-plate extends also upon three vertebrae.

Figure 11:
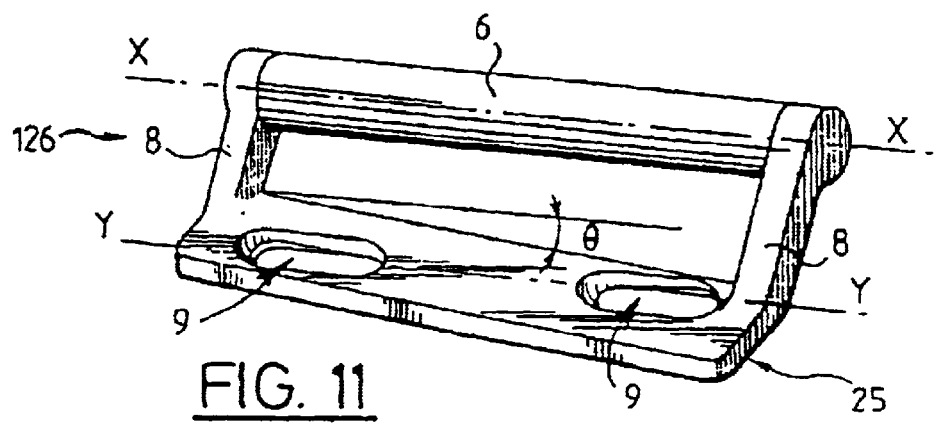
FIG. 11 is a perspective view of yet another embodiment of the present invention.

In yet another embodiment of the invention shown in FIG. 11, plate 25 is inclined at an angle (θ) in regard to the longitudinal axis (XX) of rod 6 to provide implant structure 126. Accordingly, for structure 126, while rod 6 and plate 25 are still in a side by side orientation, the longitudinal axis XX of rod 6 is oblique with respect to a longitudinal axis of plate 25. The oblong openings 9 extend, within plate 25, along to axis (YY) which is generally parallel to the longitudinal axis XX of rod 6.

It must be understood that the scope of the invention is not intended to be limited to the described elements and may include various variants. Thus the rod 6, 6' could be non-cylindrical, the inclination A of the lugs 8 to the plane of the plane of the plate 7, 7' may vary widely, in the same way as the geometry of the walls of the openings 9, 9' and of the screws 16, any profile allowing the sliding of the screws to achieve an automatic compression of a filler, e.g., an osteogenic material, a graft or the intersomatic cage being suitable. Also, in other embodiments, openings 9, 9' can be arranged without the inclined ramps 11, where compression of the graft/filler is not desired, or achieved in a different way.

In still other alternatives, the bone anchoring means of rod 16 can be different from U-shaped screws 1; for example they can be of the kind disclosed in European patent 0,612,507 or in French patent 2,692,471 (92,07,504). The intervertebral filler can be an allograft, an autograft, a xenograft, an intervertebral device or cage; another osteogenic substance to promote fusion of the adjacent vertebrae, or a combination of these just to name a few.

Many other embodiments are envisioned. For example, in yet another embodiment, a device for osteosynthesis of a spinal segment of two or more vertebrae by an anterior route comprises a rod, plate, and a connection member interconnecting the plate to the rod. The plate is disposed substantially parallel to the rod in a spaced apart relationship by the first connection member. Further, the device includes bone anchoring means for engaging the rod and the plate to the vertebrae.

In still a further form, a device for osteosynthesis of a spinal segment includes a rigid implant structure having a rod interconnected to a plate by a connection member. The plate includes a surface arranged to engage the spinal segment and the rod extends along the plate in a spaced apart relationship. The rod is further away from the spinal segment than the plate when the plate surface engages the spinal segment. A first bone anchorage element selectively contacts the rod to fasten the rod to the spinal segment. The first bone anchorage element includes a portion positioned between the plate and the rod when fastened to the rod. A second bone anchorage element selectively contacts the plate to fasten it to the spinal segment.

In yet a further embodiment, a device for osteosynthesis of a spinal segment comprises a rod, a plate, and a connection member interconnecting the rod and plate such that the plate is positioned by the connection member to extend along the rod with a surface arranged to contact the spinal segment. The connection member is inclined relative to a plane of the plate to offset the rod from the plate in a side by side, spaced apart relationship, and position the rod superjacent to the spinal segment when the plate surface contacts the spinal segment.

According to another embodiment of the present invention, a method comprises: (a) removing at least a portion of a disc between two adjacent vertebrae; (b) placing a filler between the two adjacent vertebrae; (c) providing a device comprised of a plate interconnected with a rod in a spaced apart relationship and a number of bone anchorage elements; and (d) compressing the two adjacent vertebrae with the device after placement of the filler.

According to yet another embodiment, a method comprises: (a) placing a first bone anchorage element in a first vertebra and a second bone anchorage element in a second vertebra adjacent the first vertebra; (b) providing a rod interconnected to a plate that extends along the rod and includes a first opening and a second opening; (c) engaging the rod to the first and second bone anchorage elements; (d) inserting a first bone screw through the first opening and a second bone screw through the second opening; and (e) turning the first bone screw and the second bone screw to move the first vertebra and the second vertebra closer together.

The screws, plates, and rods of the present invention are preferably made from a biocompatible material of suitable strength such as titanium, stainless steel, or such other composition as would occur to those skilled in the art.

All publications, patent, and patent applications cited in this specification are herein incorporated by reference as if each individual publication, patent, or patent application were specifically and individually indicated to be incorporated by reference and set forth in its entirety herein. Any theory of operation or finding described herein is merely intended to enhance understanding of the present invention and should not be construed to limit the scope of the present invention as defined by the claims that follow to any stated theory or finding. While the invention has been illustrated and described in detail in the drawings and foregoing description, the same is to be considered as illustrative and not restrictive in character, it being understood that only the preferred embodiment has been shown and described and that all changes, modifications, and equivalents that come within the spirit of the invention as defined by the following claims are desired to be protected.

What is claimed is:

1. Device for the osteosynthesis of a spinal segment of two or more vertebrae by the anterior route, comprising:
   a rod;
   a plate;
   a connection member interconnecting said plate to said rod, said plate being disposed substantially parallel to said rod in a spaced apart relationship by said connection member; said plate including a surface arranged to contact the vertebrae; and
   bone anchoring means for engaging said rod and said plate to the vertebrae, said means comprising at least a pair of oblong openings formed in said plate and each of said openings has a wall including a ramp adapted to slope toward a central part of said plate.

2. Device according to claim 1, wherein said connection member is a strut generally centrally located relative to said rod and said plate.

3. Device according to claim 1, wherein said plate and said rod have substantially the same length and said connection member is one of a pair of lugs interconnecting said plate and said rod to form a substantially rectangular frame.

4. Device according to claim 3, wherein said plate extends in a plane and said lugs are inclined relative to said plane to offset said rod relative to said plate.

5. Device according to claim 3, wherein said lugs are integrally formed in a single piece with said rod and said plate.

6. Device according to claim 3, wherein said rod has a first end portion and an opposite second end portion and a first one of said lugs is detachably connected to said first end portion and a second one of said lugs is detachably connected to said second end portion.

7. Device according to claim 1, further comprising means cooperative with said plate for bringing closer together adjacent ones of the vertebrae to compress a filler between the adjacent vertebrae.

8. Device according to claim 1, wherein said bone anchoring means comprises a plurality of bone anchorage elements, a first one of said elements having a U-shaped head to engage said rod and a second one of said elements having a threaded shank portion arranged to pass through an opening in said plate and a head portion arranged to engage a wall adjacent said opening, said head portion being shaped to compliment a profile of said wall.

9. A combination, comprising: a device for osteosynthesis of a spinal segment, said device including:
   a rigid implant structure including a rod interconnected to a plate by a connection member, said plate including a surface arranged to engage the spinal segment and a pair of openings formed in said plate and each of said openings has a wall including a ramp adapted to slope toward a central part of said plate, said rod being positioned to extend along said plate in a spaced apart relationship, and said rod being further away from the spinal segment than said plate when said surface engages the spinal segment;
   a first bone anchorage element operable to selectively contact said rod to fasten said rod to the spinal segment; and
   a second bone anchorage element operable to selectively contact said plate to fasten said plate to the spinal segment.

10. The combination of claim 9, wherein said connection member is a strut generally centrally located relative to said rod and said plate.

11. The combination of claim 9, wherein said connection member is one of a pair of opposed lugs interconnecting opposite end portions of said plate and said rod to form a substantially rectangular frame.

12. The combination of claim 9, wherein said rod is offset relative to said plate by said connection member.

13. The combination of claim 9, wherein said second bone anchorage element is in the form of a screw including a threaded shank portion and a head portion arranged to contact said wall and travel along said ramp when said threaded shank portion is screwed into a vertebra of the spinal segment through one of said openings.

14. The combination of claim 9, wherein said first bone anchorage element includes a U-shaped head to engage said rod.

15. The combination of claim 14, wherein said U-shaped head is threaded and further comprising a threaded plug arranged to engage said head and contact said rod.

16. The combination of claim 15, wherein said plug includes a terminal portion arranged to break-off when a predetermined amount of torque is applied to said plug.

17. The combination of claim 9, wherein said second bone anchorage element being arranged to pass through a first one of said pair of openings to engage a first vertebra of the spinal segment and further comprising a third bone anchorage element to pass through a second one of said pair of openings to engage a second vertebra of the spinal segment.

18. The combination of claim 17, wherein said first bone anchorage element engages the first vertebra of the spinal segment and further comprising a fourth bone anchorage element to engage the second vertebra of the spinal segment, said first bone anchorage element and said second bone anchorage element each including a U-shaped head to receive said rod.

19. The combination of claim 17, wherein said second bone anchorage element and said third bone anchorage element each being in the form of a screw with a head portion arranged to engage and travel along said ramp when driven through said openings.

20. The combination according to claim 17, further comprising a filler configured for placement between the first vertebra and the second vertebra.

21. The combination of claim 9, wherein said rod defines a longitudinal axis, and said plate is inclined in regard to said longitudinal axis of said rod wherein said pair of openings are oblong and extend through said plate substantially parallel to said longitudinal axis.

22. The combination of claim 9, wherein said rod and said plate extend to a length substantially corresponding to at least three vertebrae and, said plate includes a third opening wherein the three openings correspond with the at least three vertebrae, a first one of the openings being arranged for engagement by said second bone anchorage element and further comprising a third bone anchorage element arranged to engage a second one of the openings and a fourth bone anchorage element arranged to engage a third one of said openings.

23. A device for osteosynthesis of a spinal segment; comprising a rod, a plate, and a first connection member interconnecting said plate to said rod, said plate being disposed to extend along said rod by said first connection member, said plate including a surface arranged to contact the spinal segment, said first connection member being inclined relative to a plane of said plate such that said rod is offset above and lateral to said plate and positioned superjacent to said spinal segment when said surface contacts said spinal segment.

24. The device of claim 23, further comprising a second connection member interconnecting said rod and said plate, said second connection member being positioned opposite said first connection member to provide a generally rectangular frame.

25. The device of claim 23, wherein said first connection member is in the form of a strut generally centrally located relative to said rod and said plate.

26. The device of claim 23 further comprising a plurality of bone anchorage elements, a first one of said bone anchorage elements being arranged to connect to said rod and a second one of said bone anchorage elements being arranged to extend through an opening in said plate.

27. A method, comprising:

removing at least a portion of a disk from between two adjacent vertebrae;

placing a filler between the two adjacent vertebrae;

providing a device comprising: a rod; a plate; a connection member interconnecting said plate to said rod, said plate being disposed substantially parallel to said rod in a spaced apart relationship by said first connection member; said plate including a surface arranged to contact the vertebrae; and a bone anchoring means for engaging said rod and said plate to the vertebrae; and compressing the two adjacent vertebrae with the device after placement of the filler therebetween.

28. A method, comprising: placing a first bone anchorage element in a first vertebra and a second bone anchorage element in a second vertebra adjacent the first vertebra; providing a rod interconnected to a plate, the plate extending along the rod and including a first opening and a second opening; engaging the rod to the first and second bone anchorage elements; inserting a first bone screw through the first opening and a second bone screw through the second opening; and turning the first bone screw and the second bone screw to move the first vertebra and the second vertebra closer together.

29. The method of claim 28, further comprising approaching the first and second vertebrae by an anterior route.

30. The method of claim 28, further comprising: removing at least a portion of a disk from between the first and second vertebrae; and implanting a filler between the first and second vertebrae.

* * * * *